US008934606B2

(12) United States Patent
Kamireddi

(10) Patent No.: US 8,934,606 B2
(45) Date of Patent: *Jan. 13, 2015

(54) INTELLIGENT MACHINES AND PROCESS FOR PRODUCTION OF MONOCRYSTALLINE PRODUCTS WITH GONIOMETER CONTINUAL FEEDBACK

(75) Inventor: Srikanth Kamireddi, Itasca, IL (US)

(73) Assignee: Rubicon Technology, Inc., Bensenville, IL (US)

( * ) Notice: Subject to any disclaimer, the term of this patent is extended or adjusted under 35 U.S.C. 154(b) by 289 days.

This patent is subject to a terminal disclaimer.

(21) Appl. No.: 13/565,127

(22) Filed: Aug. 2, 2012

(65) Prior Publication Data

US 2013/0028385 A1 Jan. 31, 2013

Related U.S. Application Data

(63) Continuation of application No. 12/787,339, filed on May 25, 2010, now Pat. No. 8,259,901.

(51) Int. Cl.
*G01N 23/207* (2006.01)
*B23D 59/00* (2006.01)
*B28D 5/00* (2006.01)
*C30B 33/00* (2006.01)
*C30B 33/06* (2006.01)
*C30B 35/00* (2006.01)

(52) U.S. Cl.
CPC ............ *G01N 23/207* (2013.01); *B23D 59/001* (2013.01); *B28D 5/0088* (2013.01); *C30B 33/00* (2013.01); *C30B 33/06* (2013.01); *C30B 35/00* (2013.01); *G01N 2223/604* (2013.01)
USPC .......................................... 378/73

(58) Field of Classification Search
USPC ................................ 378/70, 61, 73
See application file for complete search history.

(56) References Cited

U.S. PATENT DOCUMENTS

| | | | |
|---|---|---|---|
| 2,425,750 | A | 8/1947 | McCarty |
| 2,556,167 | A | 6/1951 | Coleman |
| 3,838,678 | A | 10/1974 | Kumada |
| 4,002,410 | A | 1/1977 | Frederick |
| 4,331,452 | A | 6/1982 | Causey |
| 4,637,041 | A | 1/1987 | Brinkgreve |
| 4,649,556 | A | 3/1987 | Rinik |
| 4,788,702 | A | 11/1988 | Howe |
| 4,884,887 | A | 12/1989 | Vanderwater |
| 5,187,729 | A | 2/1993 | Ibe et al. |
| 5,405,285 | A | 4/1995 | Hirano |
| 5,484,326 | A | 1/1996 | Hirano |

(Continued)

*Primary Examiner* — Irakli Kiknadze
(74) *Attorney, Agent, or Firm* — McGuireWoods LLP

(57) ABSTRACT

The invention includes an x-ray goniometer positionable directly adjacent to processing machines used in the cutting, milling, drilling and shaping of crystal boules and crystal ingots, used in conjunction with an adjustable tilt platform capable of pitch, yaw and roll movement, allowing in-situ measurement and automatic adjustment of crystal orientation with respect to the processing machine. The goniometer may be secured to the tool or a portion of the machine which is adjacent the piece to be worked. Various embodiments include an x-ray goniometer and adjustable tilt platform incorporated into a core drilling machine, saw, surface grinder, polishing apparatus, or orientation flat or notch grinder. Incorporating an x-ray goniometer and adjustable tilt platform directly into a crystal processing machine results in a decrease in overall processing time and labor, and a significant increase in precision when processing crystal ingots into a final product, such as a notched wafer.

13 Claims, 4 Drawing Sheets

(56) References Cited

U.S. PATENT DOCUMENTS

| | | |
|---|---|---|
| 5,529,051 A | 6/1996 | Miller |
| 5,640,437 A | 6/1997 | Grueninger |
| 5,720,271 A | 2/1998 | Hauser |
| 5,768,335 A | 6/1998 | Shahid |
| 5,839,424 A | 11/1998 | Hauser |
| 5,893,308 A | 4/1999 | Katamachi et al. |
| 5,904,136 A | 5/1999 | Nagatsuka et al. |
| 5,927,263 A | 7/1999 | Muramatsu |
| 6,024,814 A | 2/2000 | Banzawa |
| 6,056,031 A | 5/2000 | Banzawa |
| 6,145,422 A | 11/2000 | Katamachi |
| 6,159,284 A | 12/2000 | Olkrug |
| 6,182,729 B1 | 2/2001 | Banzawa |
| 6,888,920 B2 | 5/2005 | Blank et al. |
| 6,977,986 B1 | 12/2005 | Beanland et al. |
| 7,072,441 B2 | 7/2006 | Beanland |
| 7,137,865 B2 | 11/2006 | Hammer et al. |
| 7,158,609 B2 | 1/2007 | Kikuchi et al. |
| 7,285,168 B2 | 10/2007 | Bradaczek et al. |
| 7,920,676 B2 * | 4/2011 | Yun et al. .................. 378/86 |
| 8,259,901 B1 * | 9/2012 | Kamireddi .................. 378/81 |

* cited by examiner

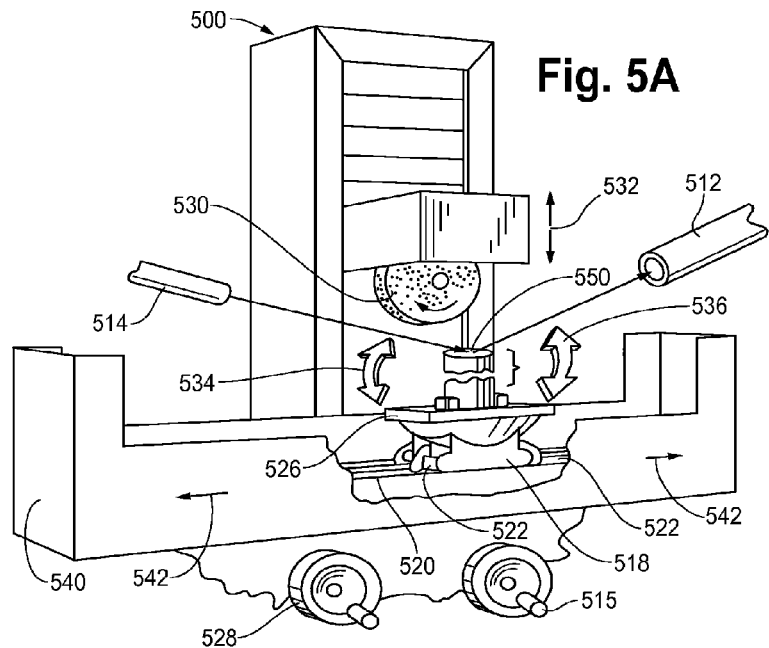
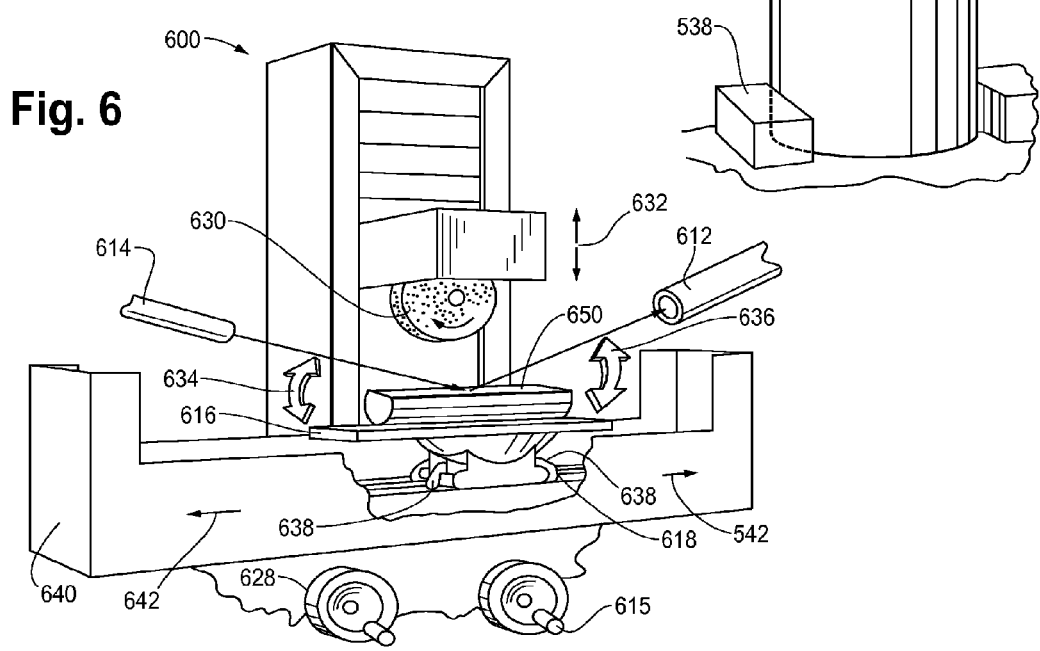

INTELLIGENT MACHINES AND PROCESS FOR PRODUCTION OF MONOCRYSTALLINE PRODUCTS WITH GONIOMETER CONTINUAL FEEDBACK

CROSS-REFERENCE TO RELATED APPLICATIONS

This is a continuation application of co-pending U.S. application Ser. No. 12/787,339, filed May 25, 2010, the disclosure of which is incorporated by reference herein in its entirety.

FIELD OF THE INVENTION

The present invention relates to the field of intelligent machines which are utilized for creating monocrystalline products wherein an orientation device, namely an x-ray goniometer, is mounted directly adjacent the machining apparatus, which utilizes an adjustable tilt platform such that immediate crystal orientation feedback and adjustment occurs both before and after processing, and at regular intervals during the creation of monocrystalline devices such as ingots, wafers and chips, in order to consistently obtain final products within close tolerances while decreasing product processing time and enhancing product quality.

BACKGROUND OF THE INVENTION

Processed crystals have increased in demand due to their usefulness as a substrate in a variety of electronic components such as gallium nitride-compound semiconductors. Such uses, however, require the crystal substrate surface to be precisely oriented. In order to achieve a precise orientation, the crystal substrate must be meticulously processed. X-ray goniometers have been indispensable in this regard, as instruments used to determine the correct crystal plane prior to processing.

An x-ray goniometer is an apparatus designed to measure the angle between crystalline orientation. It comprises an x-ray source, a collimator, a specimen, and an x-ray detector. The collimator confines the x-ray source to a narrow beam that is directed toward the specimen. As the x-rays encounter the specimen, some are diffracted toward the detector. The diffracted x-rays behave according to the Bragg Equation:

$$n\lambda = 2d(\sin\theta)$$

where lambda, $\lambda$, is the wavelength in Angstroms of the diffracted x-rays, theta, $\theta$, is one-half of the diffraction angle $2\theta$, and is the angle between the incident x-rays and the scattering planes. The distance between the crystalline lattice planes, d, is measured in Angstroms.

There are many difficulties associated with the manufacture and processing of monocrystalline materials for use in electronic devices. For example, the process begins when a crystal boule is placed on a platform and an x-ray goniometer is used to measure the orientation of the crystals. After the crystal orientation has been determined, the boule is marked and adhesive is used to rigidly and removably secure the boule to a machine fixture, in order to maintain proper orientation of the boule with respect to the drilling machine. The machine fixture commonly consists of an aluminum or graphite board. After the boule is fixed to the machine fixture and loaded into the core drilling machine, the crystal orientation is again measured to ensure that the boule has not shifted its position during the curing process for the adhesive. If the boule does not remain oriented correctly, as is often the case, it must be forcibly removed from the substrate and the process is repeated, wasting precious time and resources. This process continues until the boule is aligned and fixed properly to the substrate. Often this can take 7 to 10 repetitions or more until the boule is positioned correctly.

Once positioned correctly, the boule is then transferred to a core drilling machine, which produces cylindrically shaped ingots. The final orientation for the ingot must be accurate, within a tolerance of ±2 arc-minutes, or 1/30 of a degree. To correct for variability of crystal orientation, conventional processing will commonly produce an ingot that is substantially larger than needed. The ingots will again be measured with an x-ray goniometer and their surfaces will be ground further to produce an ingot with the required orientation. This often requires numerous measurement-grinding iterations.

What is lacking in the prior art is a system and machine assembly which does not make use of this repetitive and iterative process of drilling, grinding, or other crystal machining and still maintains proper crystal orientation throughout processing. This is accomplished by integrating the functions of crystal structure determination and automatic alignment of the crystal into the processing machine. A number of patents and disclosures relate or refer to this area and crystal processing.

The McCarty Patent, U.S. Pat. No. 2,425,750, discloses a device for aligning a crystal using light, wherein a cutting tool can replace the aligning tool after the crystal is measured. This reference does not disclose a tool using x-rays, or a tool that has both the cutting tool and the measuring tool integral to the assembly.

The Coleman Patent, U.S. Pat. No. 2,556,167, discloses a crystal analysis apparatus that has an improved jig for holding crystals while determining their orientation and facilitates easy transfer to a cutting surface. It does not disclose a device where an x-ray goniometer and cutting tool are combined into one tool.

The Kumada Patent, U.S. Pat. No. 3,838,678, discloses an apparatus where a crystal is measured with x-ray radiation and then moved onto a separate area with a cutting device at a predetermined angle. This reference does not disclose an apparatus having an x-ray goniometer which is able to measure a crystal without having to subsequently move the crystal to process it.

The Frederick Patent, U.S. Pat. No. 4,002,410, discloses a small device to removably secure a crystal in order to determine the orientation for sawing by transmitting a series of light beams and interpreting the pattern. It does not disclose a device that has an integrated measurement and sawing tool, nor does the disclosed device utilize x-rays to determine crystal orientation.

The Causey Patent, U.S. Pat. No. 4,331,452, discloses a crystal shaping apparatus having means for x-ray determination of crystal orientation and an apparatus to grind an orientation flat upon the wafer, thereby creating a crystal blank. This reference does not disclose a device with a built in x-ray crystal detection device for cutting or grinding a crystal.

The Brinkgreve Patent, U.S. Pat. No. 4,637,041, discloses an x-ray analysis apparatus with a rotatable arm for which the mutual displacement and orientation of components is executed in such a manner that it permits reproducible adjustment of the components with respect to one another. It does not disclose an x-ray analysis tool with integrated crystal processing tools.

The Rinik Patent, U.S. Pat No. 4,649,556, discloses a method and apparatus for "on-line" nondestructive measurement of grain size of various materials using a monochromatic beam of x-rays to allow actions such as corrective actions to quickly occur, and measure moving materials. It does not disclose a goniometric method of determining crystallographic orientation, or a crystal processing apparatus.

The Howe Patent, U.S. Pat. No. 4,788,702, discloses a method for determining the orientation of a single crystal which utilizes a crystal on a turntable and a stationary position-sensitive detector which is able to complete this process in a completely automated manner. This reference does not disclose a measuring device that is integrated into a processing device.

The Vanderwater Patent, U.S. Pat. No. 4,884,887, discloses a method of determining crystal orientation which uses the processing machine as a reference frame to simplify the process, and further uses a U-shaped member, which when held at a particular distance, causes the body of the crystal to come into contact with both ends of the member. It does not disclose a method which incorporates both crystal orientation determination and crystal processing in one apparatus.

The Ibe et al. Patent, U.S. Pat. No. 5,187,729, discloses a method and apparatus for determining the orientation flat of a crystal by rotating the ingot about a single axis only, using x-ray diffraction to determine the orientation, and then grinding the orientation flat. It does not disclose a method whereby x-ray analysis is integrated into subsequent polishing or cutting steps; nor does it disclose a method for crystal processing of boules or wafers.

The Hirano Patent, U.S. Pat. No. 5,405,285, discloses a machine error correction apparatus in which machine errors are measured and then transmitted into the memory of a grinding device, which uses that information to correct the errors while grinding. This invention does not disclose a grinding device combined with an orientation measurement device.

The Hirano Patent, U.S. Pat. No. 5,484,326, discloses a method for processing a crystal whereby a crystal is ground down, measured with x-rays to determine its orientation, and then subsequently ground with an orientation flat. This reference does not disclose a method where a crystal cutting or polishing process includes an integrated x-ray analysis apparatus.

The Miller Patent, U.S. Pat. No. 5,529,051, discloses a method of preparing wafers where silicon wafers are sawn from ingots on the (100) reference plane, using the reference planes to determine ingot orientation, as opposed to x-ray analysis. This reference does not disclose a method of producing crystal wafers using x-ray analysis in conjunction with a method of processing ingots.

The Grueninger Patent, U.S. Pat. No. 5,640,437, discloses a goniometer with a radiation detector, a Bragg Detector, and a fluorescent detector combined into one device. This device does not include any additional functions for cutting or otherwise processing boules, ingots, or wafers.

The Hauser Patent, U.S. Pat. No. 5,720,271, discloses a process and apparatus for orienting a crystal to a particular cutting plane by orienting it on cylinders and positioning it over a plate and then cutting it in accordance with that orientation. This device does not disclose an x-ray analysis tool with integrated crystal processing tools.

The Shahid Patent, U.S. Pat. No. 5,768,335, discloses an apparatus and method for measuring the degree of misorientation of the polished surface of a single wafer by utilizing both an optical beam and an x-ray beam to ascertain the difference between the reflected and diffracted beams with a measuring device containing a detector aligned along a track. This apparatus and method does not disclose any processing steps such as cutting or grinding being carried out by the same device that measures a crystal.

The Hauser Patent, U.S. Pat. No. 5,839,424 discloses, the use of a process and device for positioning several single crystals on a support for simultaneous cutting utilizing a machine having a rotatable frame, a gripping device carrying single crystals, a rotatable gripping support and a cutting tool. However, this disclosure does not mention or teach the use of an x-ray goniometer in conjunction with the crystal positioning and cutting device. The positioning device in the invention is outside the cutting machine.

The Katamachi et al. Patent, U.S. Pat. No. 5,893,308, discloses the use of a bonding jig which is used to bond a crystal ingot thereto prior to cutting the piece. The horizontal and vertical surfaces of the work piece bonding block may be aligned parallel to each other. The block is then fed through a wire saw. The bonding jig may be tilted to adjust the work piece so that the central axis is inclined against the cutting plane at a predetermined angle on the basis of shift value data of the crystal orientation. This disclosure does not teach orientation measurement and determination within a crystal processing machine.

The Nagatsuka et al. Patent, U.S. Pat. No. 5,904,136, discloses the use of a method and apparatus for cutting crystals which comprises a workpiece which is attached to a workpiece feed table which is fed through a wire saw, wherein the tilt angle of the workpiece has been adjusted based upon the predetermined crystal orientation outside the wire saw area. The wire saw utilizes a plurality of grooved rollers to form a wire row. The workpiece is attached to a feed table which may reciprocate with respect to the wire row. In this disclosure, however, the crystal orientation has been determined outside the crystal machining area.

The Muramatsu Patent, U.S. Pat. No. 5,927,263, discloses the use of a method for manufacturing circular wafers wherein a specified crystal orientation is detected and the crystal is then mounted upon a support table in accordance with the detected crystal orientation. Subsequently, a recognition mark is made upon the top face of the crystal in accordance with a position of the support. Finally, the support is cut and the workpiece removed. In this disclosure, however, the crystal orientation has been determined outside of the crystal processing area.

The Banzawa Patent, U.S. Pat. No. 6,024,814, discloses a method where an ingot is analyzed with a goniometer, and then removably secured to an intermediate base according to the results of that analysis, thereby properly aligning it with a saw. This patent does not disclose an apparatus or method for measuring an ingot and subsequently processing it without moving the sample in iterative intervening steps.

The Banzawa Patent, U.S. Pat. No. 6,056,031, discloses a method where an ingot is measured with an x-ray goniometer, and then transferred to an intermediate surface in a matter which preserves the information about the orientation of the crystal for later processing. It does not disclose a method of measuring and processing an ingot without an intermediate transfer from one supporting plate to another.

The Katamachi Patent, U.S. Pat. No. 6,145,422, discloses a work piece on a block which is then processed by a wire saw, and it further discloses prior art where gonio angle measuring meters are mounted on the respective wire saws. This reference does not disclose an x-ray goniometer used with grinding or other processing steps. Nor does this reference provide for continuous feedback of gonio angles.

The Olkrug Patent, U.S. Pat. No. 6,159,284, discloses a process and device for producing a semiconductor wafer by rotating a cylindrical crystal ingot along two planes of rotation, then the single crystal is secured by pads on either end of the crystal and ground to a uniform diameter. This reference does not disclose the use of an x-ray goniometer directly in association with a grinding machine.

The Banzawa Patent, U.S. Pat. No. 6,182,729, discloses the use of an apparatus for manufacturing a plurality of wafers by slicing a cylindrical ingot with a wire saw. The device consists of a measuring device for measuring crystal orientation of the ingot, and an adhering device to removably secure the ingot to an intermediate plate and a support place. This invention does not disclose the use of an orientation measuring device integrated with a crystal processing machine.

The Blank et al. Patent, U.S. Pat. No. 6,888,920, discloses the use of a low cost high precision goniometric device for use in x-ray diffractography or optical systems which comprises a spherical sector supported on at least one bearing, a top surface for mounting an object thereto, a center of rotation within an object, a rod or other member disposed below the spherical bearing surface, motors or actuators to animate the device and a linkage between the rod and the motors. This particular disclosure does not mention or teach any method suitable for determining crystal orientation during cutting, grinding or polishing processes.

The Beanland et al. Patent, U.S. Pat. No. 6,977,986, discloses the use of a lithographic tool for printing a pattern from a mask onto a wafer together with an x-ray diffraction tool for determining crystal orientation. Because the apparatus does not utilize any flats on the wafer for angular alignment purposes, it achieves a higher degree of accuracy when aligning crystal planes. Again, this particular disclosure does not teach the use of an x-ray crystal alignment device which is integral to the machine performing cutting, polishing or grinding operations upon a crystal substance.

The Beanland Patent, U.S. Pat. No. 7,072,441, discloses the use of a method of alignment for aligning crystalline substances to form lithographic features thereupon including the steps of measuring the orientation of a flat; measuring a crystallographic plane orientation of the substrate, determining an error angle; registering the flat via a lithographic tool, rotating the crystalline substance by the error angle and marking one or more features on the substance using the lithographic tool, thereby angularly aligning the feature layers to the plane orientation. However, this disclosure does not mention or teach any means for using an x-ray crystal alignment device which is integral to the machine performing a cutting, polishing or grinding operation thereupon.

The Hammer et al. Patent, U.S. Pat. No. 7,137,865, discloses the use of a method for the division of single crystals where a crystal that is to be cut into at least two parts and a cutting tool are moved relative to one another wherein the crystal will lie in the cutting plane which is characterized by an angle □ between the crystal's direction and the direction of advancement that is chosen to minimize cutting tool forces on the crystal to be cut. However, this disclosure does not teach the determination of crystal orientation in the machine utilized for processing the crystal, but rather the crystal is mounted and its orientation is determined prior to the processing step.

The Kikuchi et al. Patent, U.S. Pat. No. 7,158,609, discloses the use of an x-ray crystal orientation measuring apparatus for mounting the crystal upon a stage or platform for later processing. Again, the processing machine for the crystal does not have an orientation device which is integral to the machine.

Finally, the Bradazcek et al. Patent, U.S. Pat. No. 7,285,168, discloses the use of a method and apparatus for the determination of crystal orientation of very hard materials such as sapphire or silicon carbide. A crystal specimen is placed upon a revolving table for determining the crystal lattice orientation by rotating the table through at least one complete revolution. Subsequently a second crystal (or more) may be stacked atop the prior crystal so that multiple crystal items may be further processed at the same time. However, this particular disclosure does not teach any means for incorporating a crystal orientating device within a cutting, polishing or grinding machine.

However, nowhere in the prior art is there seen a system or assembly wherein an x-ray goniometer has been effectively incorporated into a machine which is utilized for the processing of crystalline substances in order to assure high precision alignment of the interior crystalline orientation during processing. Further, nowhere in the prior art is shown an intelligent machine which continually processes information received from an x-ray goniometer, and adjusts the crystalline substance accordingly for the purpose of ensuring proper crystal alignment during the entire process of machining a crystalline substance.

SUMMARY OF THE INVENTION

To combat the labor and time intensive inefficiencies and increase the level of precision inherent in the current state of the art, the present invention comprises a machine assembly that is capable of combining the steps of measuring the orientation of the crystal lattice planes, maintaining the proper orientation of these planes with respect to machining tools, and performing the milling/drilling/shaping procedures. It is believed that this concept will lend itself to creating a versatile platform technology which can then be applied to multiple applications.

The disclosed invention consists of a combination machine assembly incorporating an x-ray goniometer into various machines used in the processing of crystal boules and crystal ingots that also utilizes an adjustable tilt platform so that the orientation of the crystal can be measured and adjusted in situ, as well as the process for utilizing such a device. Various embodiments include the incorporation of an x-ray goniometer and adjustable tilt platform incorporated into a drilling machine used for the purpose of drilling cylindrical cores from the boule of a crystal material, an x-ray goniometer and adjustable tilt platform incorporated into a wire saw for the purpose of slicing crystal cores into wafers, an x-ray goniometer and adjustable tilt platform incorporated into the surface grinding application for all crystal forms, including cylindrical cores and wafers, and an x-ray goniometer and adjustable tilt platform incorporated into the process for grinding orientation flats and notches into a crystalline cylindrical core. Incorporating the x-ray goniometer into the processing machines, together with the use of adjustable tilt platforms, reduces the error that is introduced when ingots are transferred from one machine that measures the crystal orientation to another machine that processes the ingots and reduces errors introduced during the actual processing of the crystal. Crystal orientation can be repeatedly read and with continuous feedback, automatically adjusted if necessary to ensure the final product is within the desired tolerance level.

This is accomplished by integrating the goniometer in such a way that it can withstand the industrial conditions of the milling and drilling processes while being positioned so as to measure the crystal planes without obstructing the path of the diamond drill bit or other milling or drilling means. It is anticipated that the goniometer will be positioned such that x-rays will illuminate exactly the targeted point of the crystal to be operated upon during the various processing operations such as drilling, surface grinding, flat grinding, wire saw slicing, and the like.

The addition of an adjustable tilt platform, servomotors and feedback computer processing means that this apparatus yields a fully automated system for measuring and processing crystal materials along specified crystal planes. The crystal material is loaded and its initial position is recorded. Servomotors rotate the crystal boule a discrete amount along both the x and y axes while the x-ray goniometer produces an output signal of the intensity of diffracted x-rays corresponding to each discrete rotation. The tilt platform capable of pitch, yaw and roll movement ensures accuracy during the entire machining and x-ray determination process. The sample data must consist of an x-ray diffraction intensity reading, rotational coordinate along the positive or negative x-axis, and rotational coordinate along the positive or negative y-axis. For a specific lattice plane, the sample data is compared to the known Bragg angle and diffracted beam intensity. As the rotation continues, a two-dimensional map of the crystal lattice orientation is obtained. Using this information, the proper orientation plane is identified and the crystal is automatically adjusted using the adjustable tilt platform and servomotors to properly orient the material with respect to the machining device. Incorporating servomotors that maneuver the crystal material as it is being processed saves a great amount of time and resources in analyzing and measuring interior crystalline orientation during the processing of a crystalline substance.

Once a position of proper crystal alignment has been determined by the inventive process, the tilt platform may be locked into position for the subsequent processing step.

EXAMPLE 1

Core Drilling Application

During typical production of a sapphire crystal wafer, the outer diameter of the core must be precision ground in relation to the interior crystal orientation. The required final orientation for ingots is currently desired to be within a tolerance of ±2 arc minutes. However, with the current capability of core drills, the best tolerance attainable is only ±30 arc minutes. In the past, after drilling, shims were used in both axial directions during the surface grinding process to obtain the orientation within tolerance after numerous iterations. The cores were drilled with a larger than necessary outer diameter to provide sufficient outer material for iterative corrections, thereby wasting material and final product.

By incorporating an x-ray goniometer into a drilling machine, the goniometer may be positioned such that x-rays will illuminate the exact center point of the core to be drilled. A crystal boule is placed upon a tilt platform module, which is then positioned inside the drilling machine. Orientation of the spot marked for drilling is checked with the goniometer. Boule orientation can be automatically adjusted using the tilt platform. After the correct orientation has been verified, the tilt platform is locked into place, the goniometer is moved out of the way, and the core drill bit is positioned in its place. The crystal has been positioned exactly with respect to the axis of the drill bit. Crystal orientation can be rechecked and automatically readjusted after a predetermined number of cycles of the machine, in order to ensure that the proper orientation is maintained. For the core drilling application, orientation is rechecked and aligned for every predetermined length of infeed (for example, for every 1 inch of drilling).

EXAMPLE 2

Wire Saw Application

During typical production of thin annular wafers from a cylindrical ingot core, wafers are often sliced into thicknesses ranging from 300 to 1300 microns (0.3 to 1.3 millimeters). It is desired that the wafer surface normal be within the required orientation of ±2 arc minutes. The present preparation process involves using adhesive to removably secure a crystalline core to a beam and removably secure the beam to a base. The proper positioning of the crystalline core is of utmost importance in that it determines the final orientation of the wafer product. Correct orientation of the final product is only achieved by referencing the faces of the core with respect to the base of the wire saw apparatus. Instances in which the wafer product is required to have a relatively higher tilt angle are often associated with a higher failure rate.

With the present invention, an x-ray goniometer is incorporated into the wire saw apparatus. The goniometer is positioned such that it is capable of reading the crystal orientation of the core to be sliced after it is positioned upon the wire saw base. Appropriate adjustments can then be accomplished automatically through computer feedback processing or manually by tilting the wire saw base platform. After the core has been positioned correctly, is it then locked and the sawing process is then initiated. Crystal orientation can be rechecked and automatically readjusted at regular intervals, in order to ensure that the proper orientation is maintained. For the wire saw application, orientation is rechecked and aligned every predetermined length of infeed (for example, after grinding 100 microns).

EXAMPLE 3

Surface Grinding Machine

During typical production of a crystalline wafer, a cylindrical core of a crystalline substance must have its end flat surfaces ground in order to correct the orientation of the crystal, and often numerous time consuming iterations are required. In the past much of this process consisted of a time consuming trial and error procedure.

With the present invention, the entire process may be shortened into one simple step by incorporating an x-ray goniometer into the surface grinding apparatus such that the orientation readings of the interior crystalline configuration may be read upon the same face upon which the core will be ground. The core is automatically adjusted by utilizing a computer controlled tilt platform to which it is removably secured, after the desired target values of crystalline orientation have been determined. Then the base is locked into position and the core is ground in order to achieve the predetermined values in one simple step. Crystal orientation can be rechecked and automatically readjusted after a predetermined number of cycles of the machine, in order to ensure that the proper orientation is maintained. For the surface grinding application, orientation is rechecked and aligned every predetermined length of infeed (for example, after grinding 100 microns).

EXAMPLE 4

Orientation Flat and Notch Grinding Application

During typical production of crystalline cores often the cores are machined with a notch, groove or flat along a portion of its outer annular portion so that the subsequent users of the product may easily determine the interior crystalline configuration of any plane with respect to where it must be placed for further processing. Often after a crystalline core has been produced it is utilized in subsequent processes for slicing, lapping, edge-grinding, polishing and later, imprinting of micro-circuitry or other wafer processes which are highly dependent upon the exact positioning of the wafer surfaces with respect to their interior crystal orientation. If the alignment is not precise or high tolerances have not been achieved during the manufacture of the core, the product produced by the subsequent processor will perform inadequately, or not at all. Accordingly, the production of a highly accurate orientation notch, flat or groove along the edge of the annular core is essential to producing a high quality end product within appropriate tolerances for subsequent production procedures.

Typically orientation flat or notch for a C-axis drilled core is parallel to the A-plane. It is crucial to obtain the flat, notch, or groove with consistent orientation reading throughout its length, together with maintaining a specified flat length.

In accordance with the present invention, an x-ray goniometer is incorporated into an orientation notch, groove, or flat grinding apparatus. With this incorporation, the x-ray goniometer is able to direct the positioning of the core such that consistent readings are obtained along the length of the core, and any corrections may be easily obtained by manually twisting or moving the core into the proper position or through computer controlled adjustments of a tilt platform. After the required position has been achieved, the core is then removably secured to an adjustable tilt platform and flat grinding is then initiated in order to obtain the correct and consistent orientation readings along the length of the core. Crystal orientation can be rechecked and automatically readjusted after a predetermined number of cycles of the machine, in order to ensure that the proper orientation is maintained throughout the entire grinding process. For the core orientation flat application, the orientation is rechecked and aligned every predetermined length of infeed (for example, after grinding 50 microns).

A similar approach can be followed to grind the orientation flat or notch on individual wafers.

OBJECTS OF THE INVENTION

Thus, it is one primary object of the present invention to provide an improved system tilt platform for the processing of crystal boules, ingots and the like, whereby processing and machining time is drastically reduced while at the same time the integrity of the resulting product is significantly enhanced.

It is yet another primary object of the invention to provide a system platform for the machining of crystalline products utilizing goniometers and adjustable tilt platforms together with machining tools, which allow crystal orientation to be determined precisely and adjusted in-situ, thus providing proper orientation without timely and imprecise crystal positioning iterations between machining steps.

It is yet another primary object of the present invention to provide a system platform for the machining of crystalline products, wherein said system platform incorporates a goniometer, an adjustable tilt platform, and servomotors communicating with both the goniometer and tilt platform, such that crystal orientation information may be precisely determined in real time during processing, and adjustments to the positioning of the tilt platform may occur as rapidly as possible, thereby permitting efficient and precise machining of a crystalline material.

It is yet another primary object of the present invention to provide a tool for the slicing of crystal wafers, wherein said tool comprises a wire saw where a goniometer has been provided directly adjacent the wire saw so that the orientation of the crystal is determined as the crystal is being sliced by the wire saw, and the crystal to be processed is positioned on an adjustable tilt platform base, thereby allowing crystal repositioning as the saw may be deforming or biasing the crystal alignment.

It is yet another primary object of the present invention to provide a tool for drilling cores of crystal wafers, wherein said tool comprises a core drilling apparatus where a goniometer has been provided adjacent to the drill so that the orientation of the crystal ingot or boule is determined precisely as the crystal is being drilled by the tool, and the crystal to be processed is positioned on an adjustable tilt platform base, thereby allowing crystal repositioning as the core drill may be deforming or biasing the crystal alignment during the machining process.

It is yet a further primary object of the present invention to provide a tool for the surface grinding of crystalline products, wherein said tool comprises a grinder where a goniometer has been provided adjacent to the grinder so that the orientation of the crystal is determined precisely as the crystal is being ground into the proper formation by tool, and the crystal to be processed is positioned on an adjustable tilt platform base, thereby allowing crystal repositioning as the grinder may be deforming or biasing the crystal alignment during the machining process.

It is yet a further primary object of the present invention to provide a tool for the grinding orientation flats or notches in crystalline products, wherein said tool comprises a grinder where a goniometer has been provided adjacent to the grinder so that the orientation of the crystal is determined precisely as the orientation flat or notch is being ground into the crystal by the tool, and the crystal to be processed is positioned on an adjustable tilt platform base, thereby allowing crystal repositioning as the grinder may be deforming or biasing the crystal alignment during the machining process These and other objects and advantages of the present invention can be readily derived from the following detailed description of the drawings taken in conjunction with the accompanying drawings present herein and should be considered as within the overall scope of the invention.

BRIEF DESCRIPTION OF THE DRAWINGS

FIG. 5A is a front perspective view of a crystal ingot utilizing the present invention mounted onto an adjustable tilt platform and positioned within a surface grinder.

FIG. 5B is a front perspective view of an individual crystal ingot after surface grinding has been performed.

FIG. 6 is a front perspective view of a crystal ingot utilizing the present invention mounted onto an adjustable tilt platform and positioned within an orientation flat/notch grinding machine.

DETAILED DESCRIPTION OF THE DRAWINGS

Figure 1A:
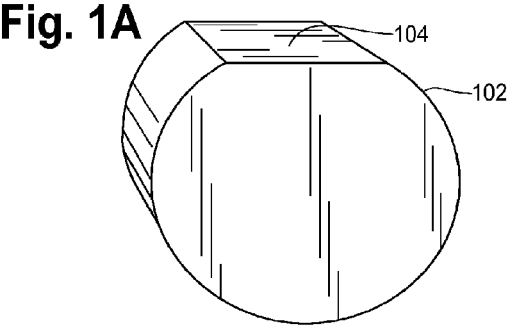
FIG. 1A is a perspective view of a crystalline core or ingot product having an orientation flat.

Shown in FIG. 1A is a crystalline core or ingot product 102 having a highly accurately positioned orientation flat 104 located along its outer diameter utilizing the present inventive process. Flat 104 has been provided to indicate the correct interior crystal alignment and configuration such that ingot product 102 may be accurately positioned into tools and jigs during subsequent operations. These annular cores are well known and utilized in the prior art. Standards for the size and type of flats have been established by numerous manufacturers desiring uniformity in use and production and such standards may be found at www.semi.org on the internet.

Figure 1B:
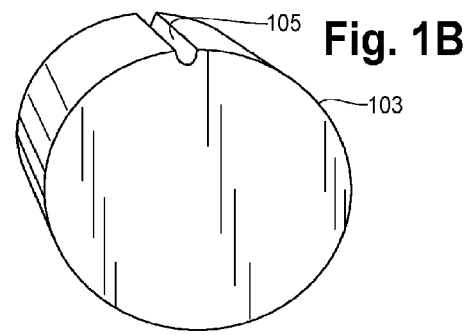
FIG. 1B is a perspective view of a crystalline core or ingot product having an orientation groove/notch.

Similarly, FIG. 1B shows a crystalline core or ingot product 103 which has been provided with a highly accurately positioned orientation groove/notch 105 located along its outer marginal portion utilizing the present inventive process. The groove/notch 105 has been machined for the purpose of indicating the correct interior crystal alignment and configuration for later processing and/or operations. This type of interior crystal orientation indication is well known and utilized in the prior art. Standards for the size and type of grooves have been established by numerous manufacturers desiring uniformity in use and production and such standards may be found at www.semi.org on the internet.

Figure 2A:
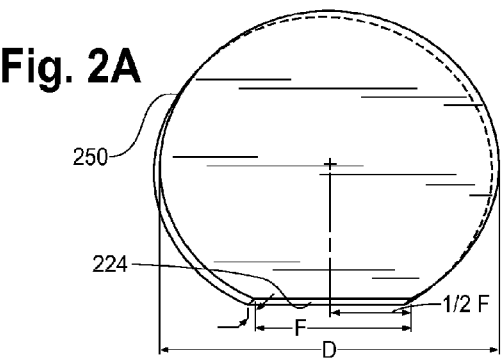
FIG. 2A is a top perspective elevation of a cylindrical crystalline wafer having an orientation flat

Shown in FIG. 2A is a crystalline wafer product 250 having a highly accurately positioned orientation flat 224 located along its outer diameter utilizing the present inventive process. Flat 224 has been provided to indicate the correct interior crystal alignment and configuration such that wafer product 102 may be accurately positioned into tools and jigs during subsequent operations. These annular wafers are well known and utilized in the prior art. Standards for the size and type of flats have been established by numerous manufacturers desiring uniformity in use and production and such standards may be found at www.semi.org on the Internet.

Figure 2B:
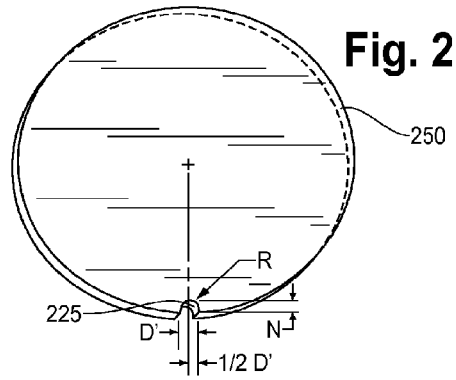
FIG. 2B is a top perspective elevation of a cylindrical crystalline wafer which has been provided with an orientation groove/notch.

Similarly, FIG. 2B shows a crystalline wafer product 250 which has been provided with a highly accurately positioned orientation groove/notch 225 located along its outer marginal portion utilizing the present inventive process. The groove/notch 225 has been machined for the purpose of indicating the correct interior crystal alignment and configuration for later processing and/or operations. This type of interior crystal orientation indication is well known and utilized in the prior art. Standards for the size and type of grooves have been established by numerous manufacturers desiring uniformity in use and production and such standards may be found at www.semi.org on the Internet.

Figure 3:
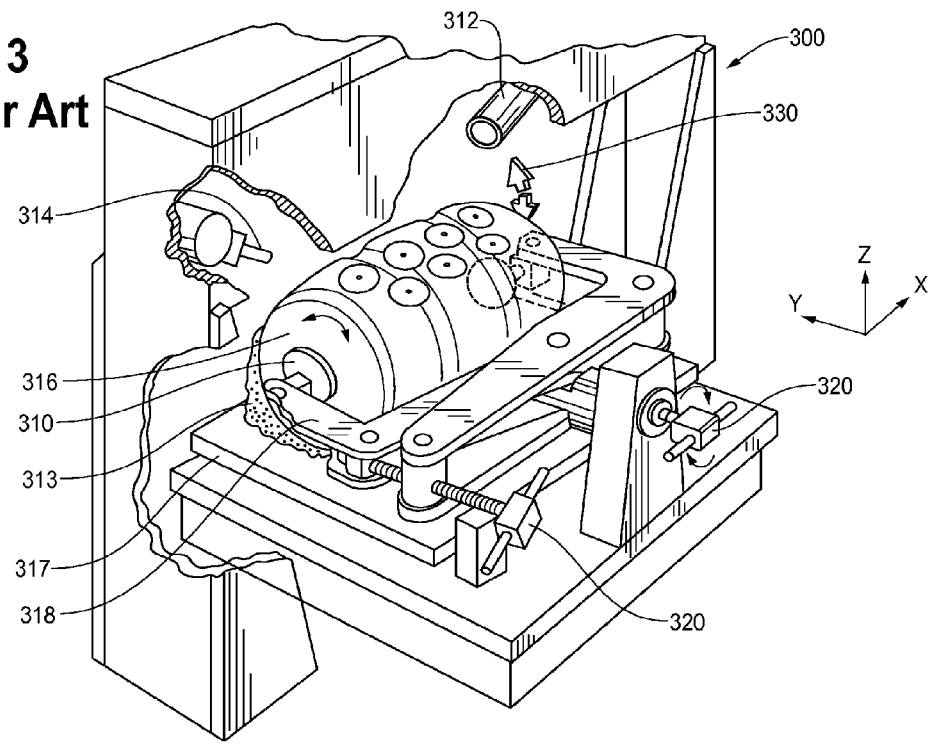
FIG. 3 is a front and left perspective view of a crystal boule mounted within a machine fixture with drilling layout (Prior art).

FIG. 3 depicts the prior art. Here crystal boule 316 is shown being removably secured to an x-ray crystal alignment apparatus 300. This apparatus consists of mounting platform 322, x-ray emitter 314, x-ray collector 312, rotating mounting plates 310, mounting clamp 318, and fixture clamp pivot 320. Crystal boule 316 is placed on a mounting platform 322 and secured using the mounting clamp 318. Using the rotating mounting plates 310 and the fixture clamp pivot points 320 the crystal boule 316 is adjusted along the radial direction 330 allowing pitch, roll and yaw. The x-ray emitter 314 and x-ray collector 312 are used to find the correct crystalline orientation of the crystal boule to be drilled. The crystal boule is manually adjusted for pitch and yaw to find the desired plane. Once the plane is identified a fine ground aluminum plate 317 is placed below the crystal boule 316 and adhesive 313 is used to hold the crystal boule to this plate. The adhesive used may be any readily available adhesive in the market. Once the adhesive dries, the crystal boule 316 with the fine ground aluminum plate 317 is moved to a milling or drilling machine for core drilling operation.

Figure 4A:
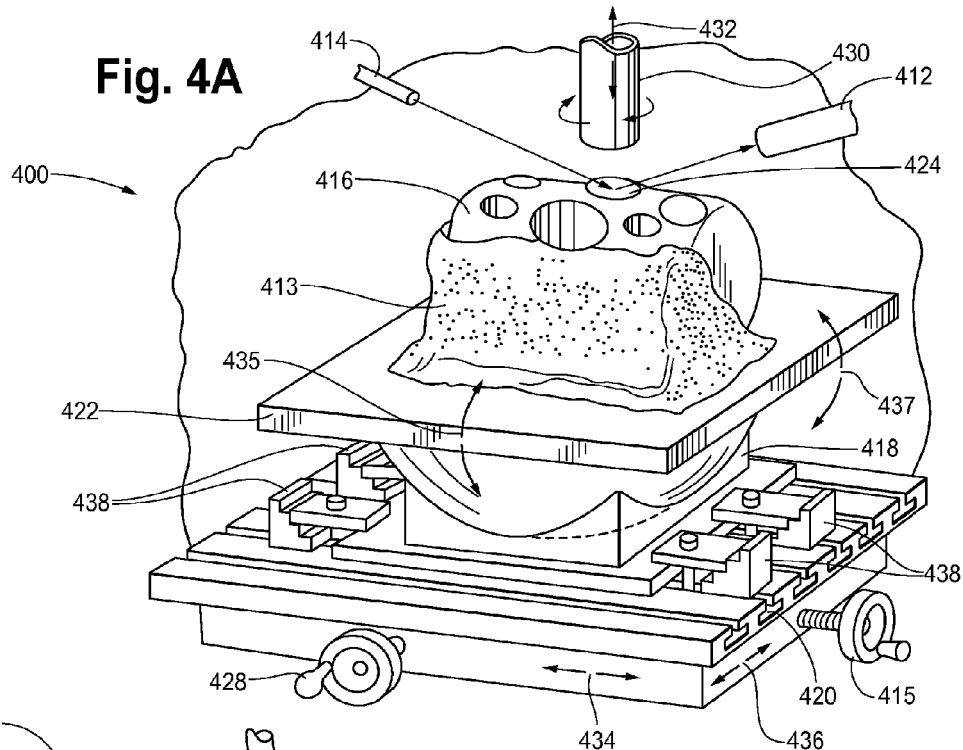
FIG. 4A is a front perspective view of a crystal boule mounted within a core drilling machine utilizing the present invention showing the boule as it has been cored.
Figure 4B:
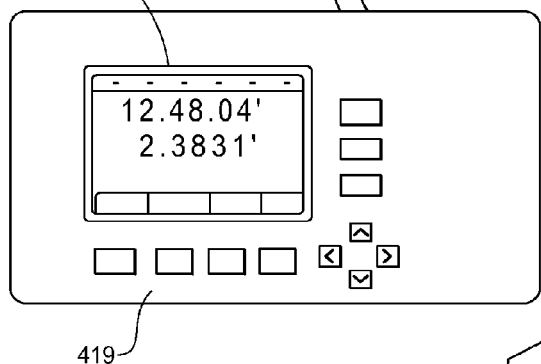
FIG. 4B is a front plan elevation of a display unit containing a computerized data processing unit for displaying the data relating to the angle of interior crystal orientation for a particular crystalline item.

FIG. 4A shows a perspective view of a core drilling apparatus 400 with an x-ray emitter 414 and an x-ray collector 412 positioned above a crystal boule 416 which allows the machine operator to easily and frequently check the positioning of crystal boule 416 at regular intervals during the core drilling process using the computer data processing unit (FIG. 4B). The output data from the collected x-rays is sent to the computer data processing unit 419 and the angle of the crystalline orientation of the boule is displayed on the LCD display 423. The crystal boule 416 is easily repositioned using a servomotor-controlled tilt platform 418. Any instances where the crystal boule 416 has moved from its proper alignment may be quickly and efficiently corrected without removing crystal boule 416 from the core drilling apparatus 400. Crystal boule 416 is removably secured in place atop mounting platform 422 using adhesive 413.

Mounting platform 422 is itself affixed to adjustable tilt platform 418, which allows crystal boule 416 to engage in yaw, pitch and roll rotations about z-axis 432, as well as tilt platform translatable y-axis 436 and tilt platform translatable x-axis 434 of adjustable tilt platform 418. Mounting platform 422 commonly comprises an aluminum or graphite board and the like, which is removably secured to adjustable tilt platform 418 which in turn is removably secured to channeled table 420 by means of bolted clamps 438. The adjustable tilt platform 418 is rotatable in roll direction 435 and pitch direction 437. Coring drill bit 430 is preferably edged with diamond powder and moves vertically along z-axis 432. For each crystalline core/ingot 450 that is desired (shown in FIG. 4C), the user must adjust the location of crystal boule 416 using x-axis turn crank 428 and y-axis turn crank 415 to move crystal boule's 416 position along the x-axis and y-axis, respectively, until the x-rays emitted by x-ray emitter 414 are aligned with core drill marking 424 as determined by the display unit. The x-ray emitter 414 emits x-rays toward crystal boule 416, which are diffracted according to Bragg's Law. Diffracted x-rays are measured using x-ray collector 412 as crystal boule 416 is rotated about rotatable x-axis 434 and rotatable y-axis 436 and the Bragg angle is determined by the computer data processing unit 419 and displayed on the LCD display 423. After the Bragg angle has been determined, crystal boule 416 is locked into place and the x-ray emitter 414 and x-ray collector 412 may be placed out of the range of slurry or other fouling debris, or alternatively, they may be shielded. Coring drill bit 430 is then lowered toward crystal boule 416 upon core drill marking 424 and crystalline core ingot 450 is formed, as shown in FIG. 4C.

This process for obtaining each cylindrical core ingot may be repeated multiple times. The checking of the position of the crystal boule 416 in relation to the core drill bit 430 is anticipated to proceed at regularly timed intervals during the core drilling process. Thus, the adjustable tilt platform 418 and channeled table 420 allows the coring drill bit 430 to drill multiple crystalline cores 450, as shown in FIG. 4C from crystal boule 416 at a plurality of desired angles while ensuring that each core ingot is oriented properly at all times.

Figure 4C:
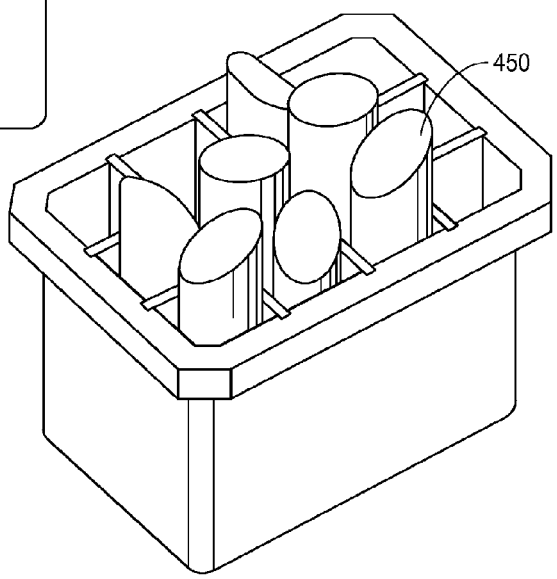
FIG. 4C is a front and top perspective view of a container housing a plurality of crystalline cores having different orientation end surfaces.
Figure 7:
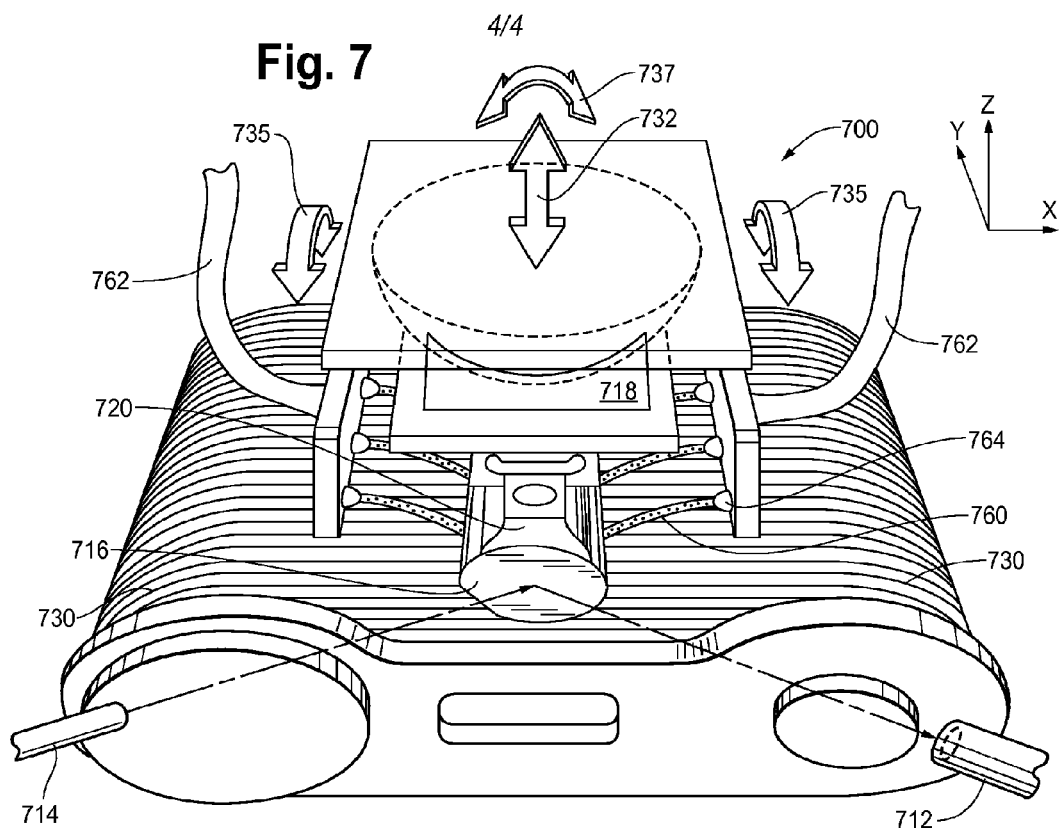
FIG. 7 shows a top isometric view of a wire saw utilizing the present invention for proper positioning of the crystalline cores to be sliced into annular wafers.

FIG. 4C shows a plurality of crystalline ingots 450 that are ready for further processing using wire saw assembly 700 shown in FIG. 7. Each of these crystalline ingots 450 may have end surfaces with angles that vary according to the customer's specifications FIG. 5A shows an ingot surface grinding apparatus 500 wherein x-ray emitter 514 and x-ray collector 512 have been mounted to the interior of the machine housing for surface grinding apparatus 500 wherein a crystalline ingot 550 may be continuously checked for proper alignment of its interior crystalline structure. An adjustable tilt platform 518 has been provided which allows the crystalline ingot 550 that is secured to the mounting platform 526 to be positioned freely and rotatably about z-axis 532, rotatable x-axis 534 and rotatable y-axis 536 as it is being machined. Turn crank wheels 528 and 515 are provided which allow the operator to manually align adjustable tilt platform 518 with respect to surface grinding apparatus 500 prior to orientation of the crystal with x-ray emitter 514 and x-ray collector 512. Adjustable tilt platform 518 is secured to a plurality of table channels 520 via bolted clamps 522. Table assembly 540 reciprocates along the table x-axis 542 and the diamond grinding wheel or similar abrasive wheel 530 machines the core in order to grind the end of cylindrical crystalline ingot 550 flat. It is anticipated that the orientation angle of crystalline ingot 550 will be checked before each pass, of after the number of desired passes.

FIG. 5B shows crystalline ingot 516 which has been secured by repositionable ingot clamps 538 which are provided on mounting platform 526 such that the crystalline ingot 516 will be stable as the end of the crystalline ingot 516 is being ground flat to the desired angle.

FIG. 6 shows an ingot flat or notch grinding assembly 600 which has been provided with 640 table assembly consisting of channels for coolant flow, grinding wheel 630 aligned with the table x-axis 642, which is intended to grind an orientation flat 650 into the aligned surface of ingot 616. X-ray emitter 614 and x-ray collector 612 have also been provided so that the orientation of the flat 650 will be accomplished with as much precision as possible. It is anticipated that the angular orientation of the ingot 616 will be checked and adjusted as needed on a periodic and regular basis, for example, with 5 passes of grinding wheel 630, or 10 passes, or 12 passes, etc. Ingot 616 has been removably secured to adjustable tilt platform 618 by means of repositionable clamps 638 provided at opposing ends thereof. Turn crank wheels 628 and 615 are provided which allow the operator to manually align adjustable tilt platform 618 with respect to ingot flat or notch grinding assembly 600 prior to automatic orientation of the crystal utilizing the x-ray emitter 614, x-ray collector 612. Adjustable tilt platform 618 also has been provided so that ingot 616 may be easily and automatically repositioned if the integral goniometer assembly consisting of x ray collector 612 and x ray emitter 614, determines that the plane orientation of ingot 616 has deviated from proper alignment during the orientation flat or notch grinding process. Adjustable tilt platform 618 may be easily and automatically positioned radially about the rotatable y-axis 636, rotatable x-axis 634, and z-axis 632 in order to reposition ingot 616 and maintain proper orientation of the crystal plane. As grinding wheel 630 descends in the direction of z-axis 632 and bears upon crystal ingot 616, grinding wheel 630 creates an orientation flat 650 in the surface of ingot 616.

FIG. 7 shows wire saw assembly 700 with crystalline ingot 716 attached to binding piece 720. Crystalline ingot 716 is movable along z-axis 732. Wire saw web 730 is arranged parallel thereto and extends along the longitudinal axis of crystalline ingot 716 at a length that is substantially greater than that of crystalline ingot 716.

X-ray emitter 714 and x-ray collector 712 analyze the crystal planes of crystalline ingot 716 by rotating crystalline ingot 716 using adjustable tilt platform 718 until a specified crystal plane is found, whereupon the position of crystalline ingot 716 is locked into place. Crystalline ingot 716 is then lowered and slurry 760 containing abrasive material, such as ground diamonds and the like is applied to the cutting area where wire saw web 730 meets crystalline ingot 716. Slurry, consisting of abrasive particles (such as silicon carbide or diamond) and oil based liquid coolant 760 is supplied via supply line 762, and exits discharge jets 764. Adjustable tilt platform 718 allows crystalline ingot 716 to be repositioned as needed, when intermittent alignment checks performed by goniometer assembly consisting of x-ray emitter 714 and x-ray collector 712 indicate improper alignment of crystalline ingot 716 with respect to wire saw web 730. This is accomplished by the ability of adjustable tilt platform 718 to automatically rotate crystalline ingot 716 about z-axis 732, rotatable x-axis 735, and rotatable y-axis 737.

Figure 8:
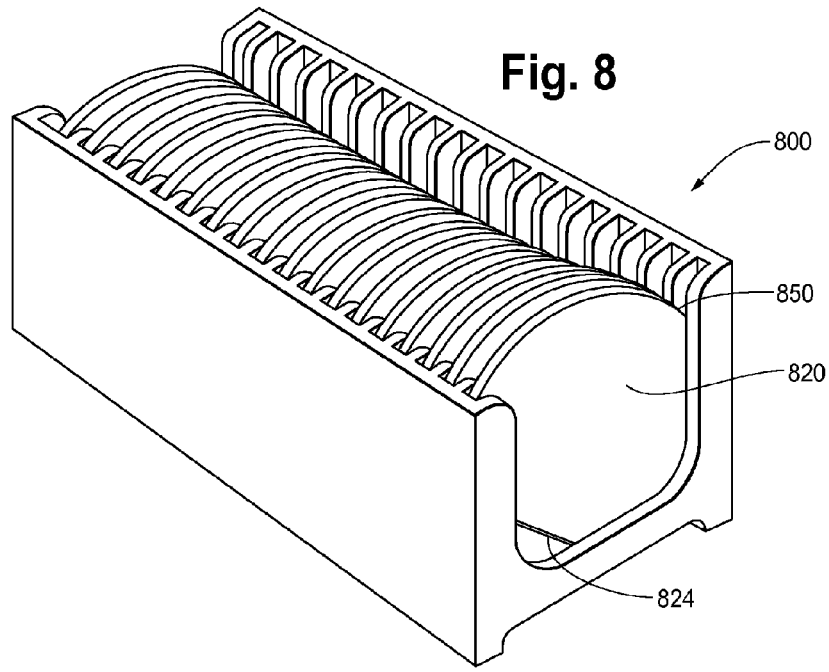
FIG. 8 shows a front top perspective view of a housing for annular wafers and a plurality of wafers being retained therein.

FIG. 8 shows wafer and housing assembly 800 with a plurality of processed crystalline wafers 850 within wafer carrier 820 as they may be delivered to the customer for further processing, or they may be further processed in house. It is vital at this step that the orientation flat 824 be as accurate as possible with respect to the interior crystal configuration or alignment of each crystalline wafer 850.

Although in the foregoing detailed description the present invention has been described by reference to various specific embodiments, it is to be understood that modifications and alterations in the structure and arrangement of those embodiments other than those specifically set forth herein may be achieved by those skilled in the art and that such modifications and alterations are to be considered as within the overall scope of this invention.

What is claimed is:

1. A machining assembly for optimizing the processing of boules and ingots, the machining assembly comprising:
   a machine tool that machines a crystalline substance;
   a tilt platform that removably secures the crystalline substance thereto; and
   an x-ray goniometer that determines alignment of the crystalline substance with respect to the machine tool,
   wherein said x-ray goniometer has been positioned substantially adjacent to said machine tool and said tilt platform.

2. The machining assembly of claim 1, wherein said crystalline substance comprises:
   a boule or an ingot.

3. The machining assembly of claim 1, wherein said x-ray goniometer module comprises: an x-ray generator and an x-ray collector.

4. The machining device of claim 3, wherein said x-ray goniometer module further comprises:
   a computerized data processing unit.

5. The machining device of claim 3, wherein said x-ray goniometer module further comprises an indicator device that indicates an interior angle position of said crystalline substance to be machined upon said platform.

6. The machining device of claim 5, wherein said x-ray goniometer module further comprises a computerized data processing unit and said indicator device comprises a display device which indicates the interior angle position provided by the computerized data processing unit.

7. The machining assembly of claim 1, wherein said tilt platform module is capable of at least one of a directional movement along the x, y and z axes, or a movement comprising at least one of a yaw, a pitch, and a roll movement.

8. The machining assembly of claim 7, further comprising servomotors capable of moving said tilt platform along the x, y and z axes, and creating yaw, pitch and roll movements.

9. The machining assembly of claim 8, further comprising a data processing unit, and said x-ray goniometer is configured to communicate crystal orientation data to said data processing unit, and said data processing unit is configured to communicate the crystal orientation data to said servomotors of said tilt platform to control orientation or alignment of said crystalline substance during processing.

10. The machining assembly of claim 8, wherein said tilt platform is configured to rotate said crystalline substance a discrete amount and the x-ray goniometer is configured to produce an output signal of intensity of diffracted x-rays corresponding to each discrete rotation, the machining assembly further comprising a data processing unit configured to receive the output signal.

11. The machining assembly of claim 8, wherein said servomotors communicate with said tilt platform and said x-ray goniometer so that crystal orientation data is determined in real time to adjust positioning of said tilt platform, thereby permitting precise machining of said crystalline substance.

12. The machining assembly of claim 1, wherein said machine tool comprises at least one tool selected from the following group: a machine drill, a machine grinder for rendering a surface flat, a machine grinder for grinding a notch in a crystalline substance, a machine polishing element for polishing a crystalline substance, and a wire saw.

13. The machining assembly of claim 1, wherein said x-ray goniometer is configured to determine interior alignment of said crystalline substance with respect to said at least one machine tool.

* * * * *